US006336136B1

(12) United States Patent
Harris

(10) Patent No.: US 6,336,136 B1
(45) Date of Patent: Jan. 1, 2002

(54) INTERNET WEIGHT REDUCTION SYSTEM

(76) Inventor: Scott C. Harris, P.O. Box 927649, San Diego, CA (US) 92192

( * ) Notice: Subject to any disclaimer, the term of this patent is extended or adjusted under 35 U.S.C. 154(b) by 0 days.

(21) Appl. No.: 09/471,297

(22) Filed: Dec. 24, 1999

(51) Int. Cl.$^7$ .................. G06F 15/16; G06F 17/00; A61B 10/00
(52) U.S. Cl. .................. 709/219; 709/227; 128/921
(58) Field of Search .................. 709/203, 205, 709/219, 229, 227; 128/920, 921; 600/300; 424/400; 705/16; 434/236, 237

(56) References Cited

U.S. PATENT DOCUMENTS

| | | | | |
|---|---|---|---|---|
| 4,318,447 A | * | 3/1982 | Northcutt .................. 177/25.19 |
| 4,576,244 A | * | 3/1986 | Zeigner et al. .................. 177/245 |
| 4,602,280 A | * | 7/1986 | Maloomian .................. 382/10 |
| 4,629,015 A | * | 12/1986 | Fried et al. .................. 177/25.19 |
| 4,686,624 A | | 8/1987 | Blum et al. |
| 4,796,182 A | | 1/1989 | Duboff |
| 4,951,197 A | * | 8/1990 | Mellinger .................. 600/300 |
| 5,055,460 A | * | 10/1991 | Friedlander .................. 514/161 |
| 5,412,564 A | | 5/1995 | Ecer |
| 5,542,420 A | | 8/1996 | Goldman et al. |
| 5,673,691 A | | 10/1997 | Abrams et al. |
| 5,722,418 A | * | 3/1998 | Bro .................. 600/545 |
| 5,774,871 A | | 6/1998 | Ferro |
| 5,796,640 A | | 8/1998 | Sugarman et al. |
| 5,839,901 A | | 11/1998 | Karkanen |
| 5,857,967 A | * | 1/1999 | Frid et al. .................. 600/301 |
| 5,876,926 A | * | 3/1999 | Beecham .................. 435/5 |
| 5,878,746 A | * | 3/1999 | Lemelson et al. .................. 600/447 |
| 5,892,856 A | * | 4/1999 | Cooper et al. .................. 382/291 |
| 5,908,301 A | * | 6/1999 | Lutz .................. 434/236 |
| 5,937,387 A | * | 6/1999 | Summerell et al. .................. 705/2 |
| 5,933,136 A | * | 8/1999 | Brown .................. 345/327 |
| 5,941,825 A | * | 8/1999 | Lang et al. .................. 600/449 |
| 5,945,107 A | * | 8/1999 | Hessel et al. .................. 424/728 |
| 5,946,659 A | * | 8/1999 | Lancelot et al. .................. 705/3 |
| 5,954,640 A | * | 9/1999 | Szabo .................. 600/300 |
| 5,967,789 A | | 10/1999 | Segel et al. |
| 6,022,315 A | * | 2/2000 | Iliff .................. 600/300 |
| 6,032,084 A | * | 2/2000 | Anderson et al. .................. 700/241 |
| 6,032,120 A | * | 2/2000 | Rock et al. .................. 705/2 |
| 6,083,006 A | * | 7/2000 | Coffman .................. 434/127 |
| 6,097,927 A | * | 8/2000 | LaDue .................. 434/308 |
| 6,153,409 A | * | 11/2000 | Bentley et al. .................. 435/69.7 |
| 6,157,337 A | * | 12/2000 | Sato .................. 341/155 |
| 6,168,563 B1 | * | 1/2001 | Brown .................. 600/301 |
| 6,190,313 B1 | * | 2/2001 | Hinkle .................. 600/300 |
| 6,199,099 B1 | * | 3/2001 | Gershman et al. .................. 709/203 |
| 6,246,967 B1 | * | 6/2001 | Libicki et al. .................. 702/101 |

OTHER PUBLICATIONS

Koa, C. et al. "A dietary recommendation expert system using OPS5", ACM Conference on Exploring Technology, pp. 658–663, 1987.*

Miksch, S. et al. "An intelligent assistant for patient care", ACM Conference on Autonomous Agents, pp. 458–465, Feb. 1997.*

Alkhalifa, A.Y. et al. "Application of the genetic algorithm to nutritional counseling", IEEE Conference on Biomedical Engineering, pp. 43–45, Apr. 1997.*

Blanchard, S.M. et al. "AIDA on–line: a glucose and islin simulator on the WWW", IEEE Conference on Engineering in Medicine and Biology Society, pp. 1159–1162, Nov. 1998.*

* cited by examiner

Primary Examiner—Zarni Maung
Assistant Examiner—Jason D. Cardone

(57) ABSTRACT

Methods and apparatus are provided for a diet system which is carried out over the Internet. A server, over a network, stores at least one weight reduction program, including information from which a specific weight reduction plan can be selected. The server receives user information, from a client, that includes a current image of the user. The server compares the current image to a previous image of the user to verify at least part of the information from the user. The server determines a weight reduction program based on the information by the user and the image comparison.

13 Claims, 6 Drawing Sheets

I NOW WEIGHT _____

BP _____

I ATE A FEW EXTRA TIDBITS (<200 CALORIES)

I ATE A FEW MEALS TOTALLY OFF THE DIET

I ATE A LOT OF EXTRA TIDBITS

JOIN SCREEN

NAME: JOE FLAT
ADDRESS: 400 POUND BLVE
CITY: FAT CITY
STATE: OHIO
ZIP: 99999
COUNTRY: USA
PAYMENT INFORMATION:
DESIRED PASSWORD:

CURRENT WEIGHT: 399
DESIRED WEIGHT: 200
HEIGHT : 5'1"

DOES YOUR COMPUTER HAVE A:

BP ☐   BODY FAT ☐   SCALE ☐   CAMERA ☐

*FIG. 4*

INTERNET WEIGHT REDUCTION SYSTEM

BACKGROUND

The present application teaches a system of carrying out a weight reduction program over the internet. More specifically, the present application teaches acquiring information about a dieting person, verifying the information, and using an expert system to analyze the information and determine a course of action for the weight reduction program.

One common organized weight reduction system requires a dieter to join a weight reduction program. Part of the weight reduction program includes counseling and analysis of the dieter's progress by a counselor. The counselor analyzes the progress based on experience of how others have reacted to similar programs.

The dieter has access by telephone, and in person, to diet counselors. The diet counselors provide encouragement and analysis, as well as setting the dieter's program. The counselor will recommend certain plans based on what works. In one weight reduction paradigm, the dieter may be obligated to buy certain meals, e.g., frozen meals or meal plans, from the weight reduction organizer. The counselor may also make up a personalized menu for each person, but again that is done by using experience.

However, the counselors often are minimally trained in recognizing the truly odd signs of medical distress during dieting. The counselors basically encourage the person to loose weight, and do that without consideration of many of the other factors that are important. Even when the user gets to see a doctor, the doctor spends only very little time looking at the user, and certainly not enough time to accurately assess their medical history.

In addition, the dieter must visit the clinic during specified hours. The dieter must obtain transport to the clinic, wait while at the clinic, and endure other burdens. This can be relatively inconvenient.

SUMMARY

The present application teaches an Internet based weight reduction program. A medical and weight reduction "expert system" is used to provide information to interface with the dieter. This can be used to determine the proper course of action for the dieter. The system acquires information about the dieter, verifies the information, and uses the information to automatically determine a weight reduction program. The system also includes a virtual counselor that allows interface with the dieter.

BRIEF DESCRIPTION OF THE DRAWINGS

FIG. 4 illustrates an initial screen that sets up an initial profile of the user.

DETAILED DESCRIPTION

Figure 1:
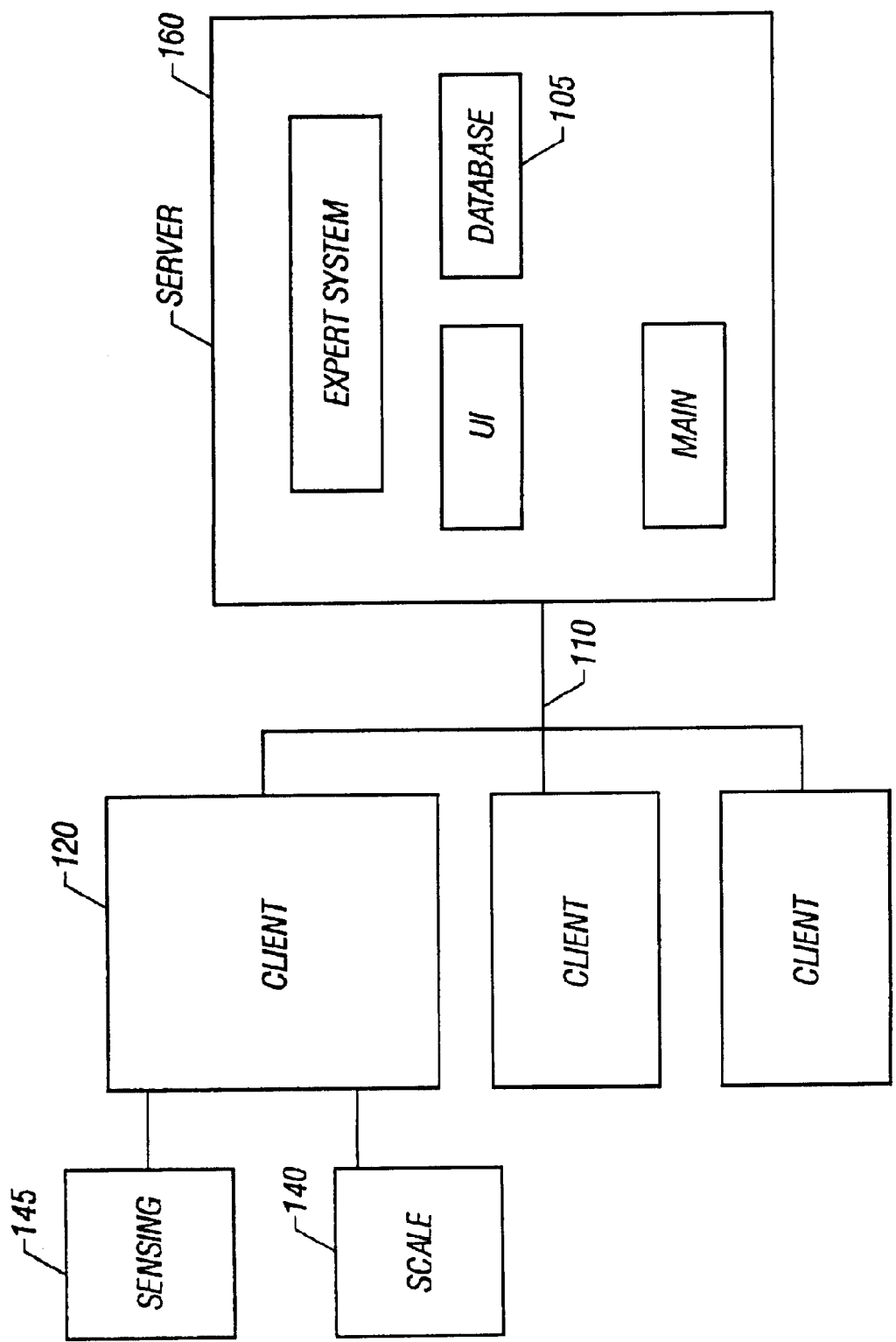
FIG. 1 illustrates a network environment such as may be used with one of the present embodiments.

The basic hardware forming the basic setup of the present invention is shown in FIG. 1. A server computer 100, at a central location, stores a database of information, as well as a user interface program, and a main program which can run a web browser. The server computer 100 is connected to a network 110, which connects the server 100 to a plurality of client computers. The network can be the Internet, or can be any other network that allows an exchange of information. For example, in one embodiment, the network 110 may be a dedicated dial-up or LAN network. The network comprises at least an information line, and a router 130. The information line 125 can be a telephone line and the router 130 can be the internet backbone, for example. The server computer 100 runs a routine that is described with reference to the flowchart of FIG. 2.

Many client computers can be connected to the server 100. Client 120 is shown at a remote location.

The client computer 120 can be any computer which is capable of running a network interfacing program such as a web browser. In addition, the client computer can have various peripherals attached thereto. These peripherals can include, for example, a camera 135, an electronic scale 140 and/or an alternative body sensing part 145. Desirable body sensing parts 145 include an electronic blood pressure measuring device which produces an electronic output indicative of blood pressure, an electronic blood sugar reader, an electronic body fat sensor, or other know electronic sensors which measure any parameters related to body size or fat can be used.

In operation, each of the server computers is driven to run the specified routine under control of the server.

According to the present application, the dieter enters an initial profile, either over the network, e.g., the Internet, or in person. The profile may be supplemented by a physical examination by a real physician. This initial profile is used as the baseline. Later operations can carry out totally remotely, e.g., over the internet, using the expert system and a virtual diet counselor or "V-counselor".

Clinic-based systems typically allow the dieter only limited visits to a counselor, e.g. once a week. However, the counselor is often an important part of the diet, since the counselor provides encouragement for the user on the diet.

The present system uses a "virtual" counselor. The counselor is programmed with information and responses that are based on the same training as the training that is obtained by the real counselor. For example, the v-counselor is programmed with responses to situations. Much information and training is known for such counselors, so just an example will be provided.

The user tells the counselor how they have done in the past week, using the form given herein. If the user has lost an expected amount of weight in an expected amount of time, the user is told that their body is reacting well to this regiment and to keep up the good work. If the user has not lost much weight, the user can be given an encouraging message, such as "don't feel discouraged, you didn't do anyhting wrong, your body is at a plateau." If the user has cheated on the diet, they are told, again, "That's ok, but let's get to the root of why you cheated. What triggers proplpted you to go off the diet, and what can we do to avoid those triggers?".

Since the v-counselor is availible all the time, the user can report to the v-counselor more often, e.g., right after cheating, when the trigger might be fresher in the dieter's mind.

The v-counselor is therefore an effective substitute for a real counselor. Unlike the real system which has limited access, however, the present system allows the dieter to see the counselor with any desired regularity. Since the visits are virtual, the counselor can be visited any number of times each day. Also, the virtual counselor is equipped with a question and answer database, e.g., like the question and answer database used by internet search engines. This allows asking any desired question to the virtual counselor, and obtaining an answer to the question.

The system also uses a medical expert system. The virtual counselor is armed with the entire capability of the expert system. What that means, effectively, is that the dieter can receive expert care, 24 hours a day.

It is common among obese people, especially those who are excessively overweight, to exaggerate their progress on a diet. For example, a person may lie about their weight, because it makes them feel better about themselves. Unfortunately, this may defeat the ability of the expert system to make proper diagnosis. Accordingly, one aspect of the present application teaches verification of the entered information.

Another aspect addresses liability. The expert system is still just a computer. Hence, one aspect of the system provides a case analysis of each of the patients to be reviewed by a live physician. The physician can sign-off on each case.

Figure 2:
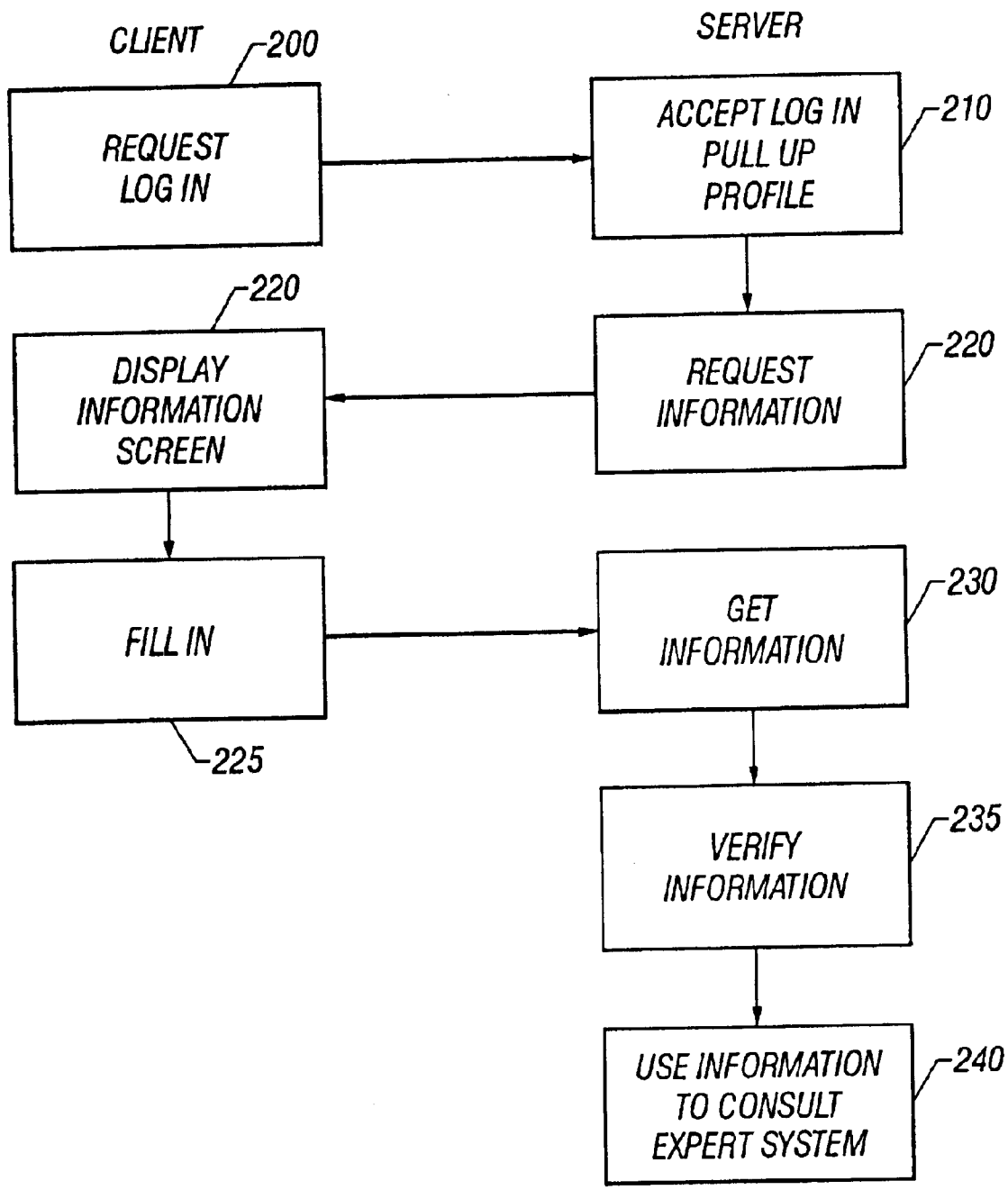
FIG. 2 is a flow chart of the client/server interactive steps.

The specified routines run by both the client and server computers are shown in FIG. 2. It should be understood, however, that multiple client computers could simultaneously operate. When this happens, this client part of the routine, shown on the left in FIG. 2, may have multiple clients requesting information from the same server. Any multitasking system can be used to handle these requests.

FIG. 2 shows the operation. At step 200, the client computer 120 transmits a log on request to the weight reduction network operating on the server computer. This can be done by entering a user name and password. Alternatively, biometric information can be obtained from the part 145 and sent to the client computer. The biometric information part uniquely identifies the dieter, and hence serves as the log-in.

At step 210, the server computer recognizes an accepted dieter. In response to this detection, the server obtains the pre-stored profile of the user. The pre-stored profile includes information that was entered to enroll the person into the weight reduction system and also information from previous system accesses. Each time the user accesses the weight reduction system, additional information can be added to the pre-stored profile and stored in the main database 105 in server 100.

At step 120, the server prepares an information screen to present to the dieter. This information screen uses the virtual counselor to request information from the dieter about how they have been doing since the last visit date 304. The initial information screen is shown in FIG. 3. The virtual counselor 300 is shown asking a question. The salutation of "Hi, Dieter" is filled in with the personalized name from the users profile, in field 302.

This system relies on the dieter telling the truth about how they have been doing. The counselor asks the dieter if they have been following the regulated diet since the last session. The options are yes (totally), only partially, or no, not all. One of the boxes must be checked to proceed. Each of these different options brings up different information on the rest of the screen.

The "no" box would be checked if the dieter had decided for one reason or another to abandon the diet totally for all or part of the week. This brings up the menu shown in FIG. 3B, which shows some common reasons. A special occasion might be selected to signify a wedding, a holiday or the like. Other reasons include "diet was too hard", indicating than a less aggressive weight reduction plan should be selected. If the user selects "I didn't feel good," then the dieter is told to see a physician, or in the kiosk embodiment, can be immediately sent to a physician.

If none of the selected options apply, then the user is asked to fill-in an option, under the "other".

Figure 3A:
FIGS. 3A–D illustrate various information screens of the system
Figure 3B:
Figure 3C:
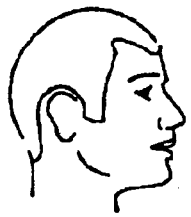

If the dieter selects yes totally in FIG. 3A, the dieter's vital information is obtained from the screen of FIG. 3C. This vital information can include at least the dieter's current weight. The blood pressure of the user, blood sugar, ketosis level, or other additional information can also be entered in FIG. 3C. Each of these options are optional.

Figure 3D:
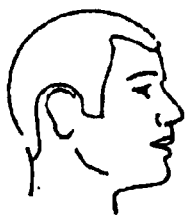
Figure 3D:
Figure 3D:
Figure 3D:

FIG. 3D shows the screen that is used when the dieter indicates that they only partly followed the diet. The dieter can select between "a few extra tidbits", "a lot of extra tidbits", or "a few meals off the diet."

After either FIG. 3B or 3D, the information screen of FIG. 3C is brought up, filled in at 225, and information is supplied to the server.

At step 235, the server verifies the information that has been obtained. This can be done by using weight from the scale 140, to determine if the user has lost weight, or at least, not gained any weight.

Alternatively, camera 135, attached to the computer, can be used to obtain an image of the user. The image is compared to previous images to determine if the user appears to be losing any weight. For example, if the user continually indicates that they are losing weight, then the image that is obtained should have somewhat less body size then a previous image. This can be measured as a ratio of waist size, for example. The user can be requested to wear tight fitting clothing, so that an accurate image can be obtained. The image can be obtained by requesting the user to "stand up so that image can be obtained". The image is obtained and compared with previous images. This provides some verification that the user is telling the truth about their progress on the diet.

Alternate means of verification besides those described above can also be used. The verification element can include an element that senses various body parameters. For example, devices which test body fat amount are well known. A body fat amount tester such as described in U.S. Pat. No. 5,941,825 can be attached to a computer input port. Alternatively, a blood sugar tester can be used to test blood sugar.

Any other means which can be attached to the computer, and which provides an electrical signal that can be decoded by the computer and used to verify the information, can alternatively be used. For example, the scale can produce an electrical output which can be coupled into the computer.

At step 240, the server consults the expert system using the information that has been obtained, to determine, if everything is within tolerances. For example, if the user has lost too much weight, this may be a signal that the diet used was too aggressive or even an indication of a medical condition. Therefore, a less aggressive diet can be selected or, in extreme cases, the dieter is told to see a doctor. If the user has lost an expected amount of weight, then the aggressiveness of the diet used in the past week is probably about right, and a similarly aggressive diet can continue to be used. Finally, if the user has not lost as much weight as expected, a more aggressive diet can be used. While this embodiment explains how different multiple levels can be used, it should be understood that more than just three gradations of the diet can be used.

The expert system selects a weight reduction program based on the selected gradation, and on previous weight reduction programs that have been provided.

The weight reduction plans can be dispensed in any desired form. In one form, the weight reduction plans are dispensed as menus to be followed by the user. In another form, the weight reduction plans are dispensed as pre-made meals, easy frozen or freeze dried, that are either sent to the user or can be picked up by the user. In the kiosk embodiment, after the user visits the kiosk, the meals can be immediately available.

During initial set up, described in further detail herein, a number of different weight reduction plans are defined. Like any of the established weight reduction plans, many different weight reduction plans, each comprising a complete meal. These weight reduction plans can each be for a specified period of time, e.g., for between two days and 14 days. The weight reduction plans each fall within a level, representing an amount of aggressiveness of the plan. The aggressiveness of the weight reduction plan is reflected in the meal plans that are selected. For example, a more aggressive weight reduction plan may have fewer calories, or more fat burning substances. A less aggressive weight reduction plan may have less. The way in which these weight reduction plans are formed is well known by those of ordinary skill in the dietician art. Companies such as "Weight Watchers™ and Jenny Craig™ have many different scientifically-determined plans, for example. Also, weight reduction plans are described in U.S. Pat. No. 5,945,107, for example.

Other features of this system include an initial membership initiation screen which sets up the initial profile. The initiation screen is shown in FIG. 4. The user enters their name and vital statistics—height, weight, desired weight, address, payment information, user name, password, etc. The user also indicates peripherals that are attached to the computer.

In a preferred mode, at least one peripheral which can verify some aspect of what the user-entered information is attached to the computer. Allowable peripherals include a digital camera, a scale, a blood pressure indication sensor, a body fat detector. If the electronic camera is the peripheral, then the camera acquires an image of the person as part of the sign in. In this embodiment, the image obtained by the web camera can be annotated according to the user profile to provide a simulated image of what the user will look like after losing the desired amount of weight.

An image of the user is obtained. That image is correlated to determine the user's body shape that shows a specified body shape. A database within also stores a plurality of different specified body shapes. Each specified body shape represents a person's size and weight, and can be taken, for example, from a real person. For example, body shapes of persons who are 5 feet 3 inches tall can be taken for each of a plurality of weights, e.g., at 5 pound increments. The same can be done for 5 feet 4 inch tall people, 5 feet 5 inch tall people, etc. This may require obtaining 100–200 images as an initial set up. However, once set up, the same body shapes can be used by all clients.

When an initial body shape is obtained by the web camera, it is correlated across all the images in the database, to determine the closest fit to an image in the database. The image to which the obtained image most closely corresponds can also be used as an additional method of verification. For example, if the user states that they are a certain height and weight, this should be at least close, e.g., within 20 to 30% of, the image in the database representing that body style.

The differences between the images can be found and used as an additional verification. If this, or any of the other verification techniques are found to be negative, then the verification fails. A response to a failed verification can include requiring the dieter to go to see a live counselor or doctor or simply setting a flag which indicates that there is less confidence in that information. An important part of the operation can be based on the verification that is carried out by these peripherals.

If an electronic scale is used, then the output of the electronic scale is directly coupled into a port of the computer, e.g., the USB port or the serial port. That weight is displayed on the screen and also used as information by the computer. It is later directly sent to the weight reduction company. This is perhaps the best way of verifying the information. Each time the user steps on the scale, which may be several times a day, their weight information can be stored in the computer when it is displayed, along with the time and date. This can be used to produce a graph of the weight information. The server computer can also store this information.

Verification can alternately use a computer-based camera. This has been briefly discussed above. An outline of a person's shape is determined by obtaining an image of the person, and correlating across the image to determine the person's basic body shape. That basic body shape is then stored as a reference. Later basic body shapes can be normalized to the original image, e.g., by equalizing head sizes. These normalized images should be the same or smaller than the original basic body shape. If, for example, the user alleges that they have lost 10 pounds, then that can be verified, over time from the image of the body shape. Therefore, a camera can be used as a verification mechanism. The camera can also be used to obtain real time measurements of the person's size, and again provide a graph of size as a function of time/date. The camera can also be used for a videoconference function if communication with a live counselor or doctor becomes necessary. One alternative is to automatically connect with a live counselor or doctor when necessary.

The body fat measurement device described above can be used to produce similar results.

A first embodiment that has been disclosed above uses the system over a network, e.g., the internet.

Figure 5:
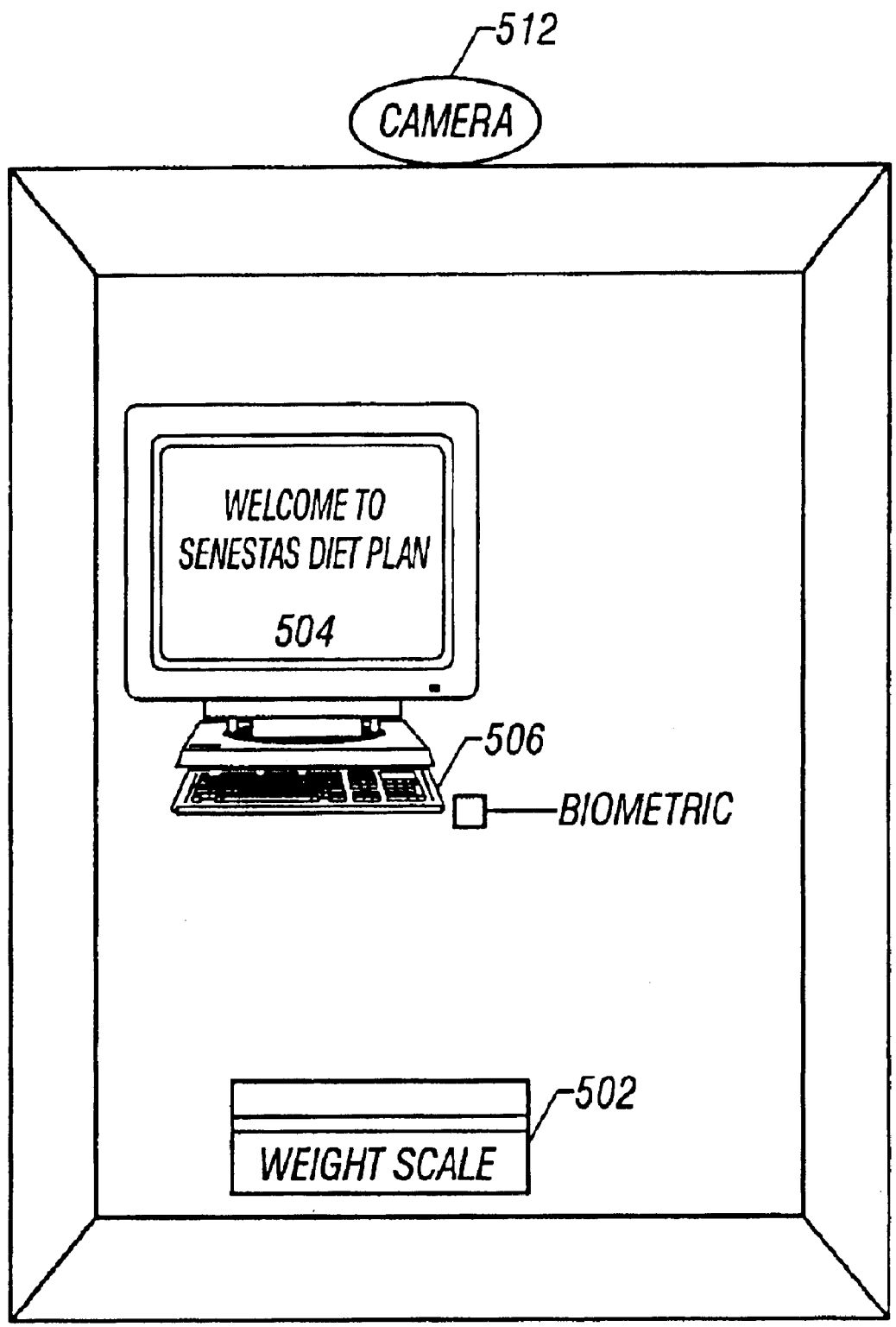
FIG. 5 illustrates a kiosk model to be used by one of the embodiments of the invention.

A second embodiment, which operates using a kiosk model, is shown in FIG. 5. In this embodiment, an unattended kiosk 500 is located in a retail location, e.g., in a drug store, health food store, grocery store, etc. The kiosk 500 includes a floor-mounted scale 502, a display 504, keyboard entry device 506, cuff 510 (for blood pressure/heat rate), and camera 512. The dieter stands in the kiosk as shown. A chair can be placed in the kiosk on the scale for a sitting version.

The user logs in at the kiosk, which automatically obtains weight and image information, and carries out the electronic diet as described above. Then, the prescribed diet slip is either printed for the dieter, or sent to a stock-person at the store who gets the diet material. For instance, frozen diet meals can be sold for each of the diet plans.

Although only a few embodiments have been described in detail above, other modifications are contemplated.

What is claimed is:

1. A method of conducting a weight reduction program over a network, comprising:

storing, on a server computer of the network, information related to at least one weight reduction program, including information from which a specific weight reduction plan can be selected;

obtaining information from a user related to the weight reduction program in a client computer, said obtaining information comprising obtaining a current image of said user, sending said information from said client computer to said server comouter;

comparing said current information about said user with previous information about said user, by determining a current outline of a user represented by said image as said current information, comparing said outline with a previous outline representing said previous information, to determine a relationship between said current outline and said previous outline;

using said relationship to verify at least part of said information in said client computer; and determining, in said server computer, a weight reduction program plan based on information obtained by the client computer and said relationship.

2. A method as in claim 1, further comprising storing an initial user profile.

3. A method as in claim 2, wherein said initial user profile includes a starting weight and a desired weight.

4. A method as in claim 3, wherein said client computer includes an electronic camera attached thereto, and further comprising obtaining an image of the user with said camera;

annotating said image to simulate a weight loss; and displaying an annotated image.

5. A method as in claim 4, wherein an annotated image is a simulated picture of the user having lost said amount of weight.

6. A method as in claim 1, further comprising providing identity information from the client to the server, wherein the server obtains a user's profile from said identity information.

7. A method as in claim 6, wherein said identity information is via biometrics.

8. A method as in claim 1, wherein said client and said server are connected over the Internet.

9. The method as in claim 1, wherein said verifying comprises automatically obtaining a weight of the user.

10. An apparatus comprising a machine-readable storage medium having executable instructions for entering diet related information to a remote server computer from a client computer, the instructions enabling the client computer to:

obtain information from a user;

send said information to a remotely-located client computer;

receive information about weight reduction based on said information from said user;

display said information about weight reduction on said client computer; and wherein said Instructions further enable the client to verify information that is entered by said user by obtaining a current image indicative of said user, and determining a current outline of a user represented by said image, and comparing said outline with a previous outline representing said previous information, to determine said relationship, said relationship being based on said current outline and said previous outline; and using said relationship to verify at least part of said information in said client computer.

11. An apparatus as in claim 10, wherein said instructions further enable the client to measure a parameter related to weight for said verify of said information.

12. An apparatus as in claim 10 wherein said instructions enable the computer to automatically determine a fat content of the user to verify said information.

13. A method of conducting weight reduction, comprising:

storing weight reduction information on a server;

manually entering information into a client;

accessing the server using information from the client to obtain information from the server indicating a recommended weight reduction procedure based on said information from the client; and obtaining current information about said user including a current image of the user, and determining a current outline of a user represented by said image, and comparing said outline with a previous outline representing said previous information, to determine a relationship between said current information and said previous information, to verify at least part of said information in said client computer.

* * * * *